United States Patent
Sanina et al.

(10) Patent No.: US 8,067,628 B2
(45) Date of Patent: Nov. 29, 2011

(54) WATER-SOLUBLE BINUCLEAR NITROSYL IRON COMPLEXES WITH NATURAL ALIPHATIC THIOLYLS POSSESSING CYTOTOXIC, APOPTOTIC AND NO-DONOR ACTIVITY

(75) Inventors: Natalia Alexeevna Sanina, Moskovskaya obl. (RU); Konstantin Alexandrovich Lysenko, Moscow (RU); Olga Stepanovna Zhukova, Moscow (RU); Tatyana Nikolaevna Rudneva, Moskovskaya obl. (RU); Nina Sergeevna Emelianova, Moskovskaya obl. (RU); Sergei Mikhailovich Aldoshin, Moskovskaya obl. (RU)

(73) Assignee: Institute of Problems of Chemcial Physics RAS (IPCP RAS), Moskovskaya Obl. (RU)

( * ) Notice: Subject to any disclaimer, the term of this patent is extended or adjusted under 35 U.S.C. 154(b) by 38 days.

(21) Appl. No.: 12/602,867

(22) PCT Filed: Jun. 2, 2008

(86) PCT No.: PCT/RU2008/000338
§ 371 (c)(1),
(2), (4) Date: Jan. 28, 2010

(87) PCT Pub. No.: WO2009/148346
PCT Pub. Date: Dec. 10, 2009

(65) Prior Publication Data
US 2010/0190850 A1 Jul. 29, 2010

(51) Int. Cl.
C07F 15/00 (2006.01)
A61K 31/295 (2006.01)
(52) U.S. Cl. ........................................ 556/146; 514/502
(58) Field of Classification Search .................. 556/146; 514/502
See application file for complete search history.

(56) References Cited

OTHER PUBLICATIONS

Dillinger et al., Dalton Transactions, pp. 3562-3571 (2007).*
Janczyk et al., Nitric Oxide, vol. 10, No. 1, pp. 42-50 (2004).*

* cited by examiner

*Primary Examiner* — Porfirio Nazario Gonzalez
(74) *Attorney, Agent, or Firm* — Osha • Liang LLP (57) ABSTRACT

The present invention relates to water-soluble binuclear cationic nitrosyl iron complexes with natural aliphatic thiolyls of general formula $[Fe_2(SR)_2(NO)_4]SO_4$,
wherein R is sulfur-containing aliphatic ligands of natural origin, preferably, cystamine or penicillamine, to a method for the preparation thereof, to use thereof as an anticancer agent, to an apoptosis inducer, to a pharmaceutical composition comprising said complexes in an effective amount, and to a kit useful for the treatment of cancer diseases.

13 Claims, 7 Drawing Sheets

WATER-SOLUBLE BINUCLEAR NITROSYL IRON COMPLEXES WITH NATURAL ALIPHATIC THIOLYLS POSSESSING CYTOTOXIC, APOPTOTIC AND NO-DONOR ACTIVITY

TECHNICAL FIELD

The invention relates to water-soluble binuclear nitrosyl iron complexes and it is useful in medicinal practice for the development of new generation medicaments for treating cancer diseases.

BACKGROUND OF THE INVENTION

In recent years in order to develop medicinal preparations of a new generation for use in the therapy of oncological diseases, an intensive search is being carried out for anticancer agents based on complexes of transition metals with an improved activity spectrum and reduced side effects as compared with already used clinical preparations, for example, cisplatin, sodium nitroprusside and the like.

The use of NO donors as a new class of anticancer agents is associated with the important role of NO in the process of growth of malignant neoplasms [Wink D., Vodovoz J., Cook J., Biochemistry, 1998, 63, 7, pp. 948-957]. Nitric oxide was shown to change the level of apoptosis of the tumor cells, the activity of the p53 gene and neoangiogenesis [Brune B., Schenederhan N., Nitric oxide evoked p53-accumulation and apoptosis, Toxicol Letters, 2003, 193, 2, pp. 19-23], to suppress the activity of a key reparation protein $O_6$-methyl-guanine-DNA-methyl-transferase of mammals [L. Liu, M. Xu-Welliver, S. Kanagula, H. E. Pegg, Inactivation and degradation of $O_6$-alkylguanine-DNA alkyltransferase after reaction with nitric oxide. Cancer Res., 2002, 62, pp. 3037-3043]. However, the currently known synthetic NO-donors of different classes (organic nitrates, diazonium diolates, nitrosothiols and others) are not used as clinical therapeutic agents for treating cancer diseases but they are only used to enhance (to a different degree depending on chemical nature) the effect of existing chemotherapeutic agents or radiotherapy [Wink D., Vodovoz J., Cook J., Biochemistry, 1998, 63, 7, pp. 948-957; N. P. Konovalova, S. A. Goncharova, L. M. Volkova, T. A. Raevskaya, L. T. Eremenko, A. M. Korolev, Nitric Oxide: Biology and Chemistry, 2003, 8, pp. 59-64; Yang, W., Rogers P. A., Ding H., J. Biol. Chem., 2002, 277, pp. 12868-12873; 0. Siri, A. Tabard, P. Pullumbi, R. Guilard, Inorg. Chim. Acta, 2003, 350, p. 633; J. L. Burgaud, E. Jngini, Del Soldato P. Ann, N.Y. Acad. Sci. 2002, 962, p. 360; T. I. Karu, L. V. Pyatibrat, G. S. Kalendo, Toxicology Letters, 2001, 121, p. 57].

On the other hand, in the last 15 years, nitrosyl iron complexes with sulfur-containing ligands have been reliably established as one of the natural forms of natural reservoirs of NO. Such compounds are formed in cells as a result of endogenous NO effect on active sites of non-heme iron-sulfur proteins [Butler A. R., Megson I. I., Chem. Rev., 2002, 102, pp. 1155-1165] and they are cellular NO "depot". Binding NO to active sites of metal enzymes, in particular to non-heme iron-containing proteins is being extensively studied [Ford P. C., Lorkovic L. M., Chem. Rev., 2002, 102, 993; Hoshino M., Layeran L. E., Ford P. C., Coord. Chem. Rev., 1999, 187, p. 75]. Their synthetic models (Roussin's "red salt" esters) have the following formula $[Fe_2(SR)_2(NO)_4]$, wherein R is Et, t-Bu, $(CH_2)_4$—$CH_3$, $C_6H_5F$, Ph [T. Thomas, J. H. Robertson, E. G. Cox, Acta Crystallogr., 1958, 11, p. 599; C. Glidewell, M. E. Harman, M. B. Hursthouse, I. L. Johnson, M. Motevalli, J. Chem. Res., 1998, 212, p. 1676; R. E. Marsh, A. L. Spek, Acta Crystallogr., Sect. B. Struct. Sci., 2001, 57, p. 800; C. Jinhua, M. Shaoping, H. Jinling, L. Jiaxi, Chinese J. Struct. Chem., 1983, 2, p. 263; T. B. Rauchfuss, T. D. Weatherill, Inorg. Chem., 1982, 21, pp. 827-830.]. These binuclear diamagnetic sulfur-nitrosyl complexes of μ-S type with R=Alk generate NO upon thermo- or photo-activation [J. L. Bourassa, P. C. Ford, Coord. Chem. Rev., 2000, 200-202, pp. 887-900] and may serve as new promising anticancer NO-donor agents. In the article by A. Janczyk et al. Nitric Oxide, 2004, 10, 1, pp. 42-50, the direct cytotoxic effect of a nitrosyl iron complex $Na[Fe_4S_3(NO)_7]$ on the human and mouse melanoma cells has been studied for the first time. However, this nitrosyl iron complex generates NO upon photoactivation only, and it cannot be used as an anticancer medicament because of the high toxicity with regard to normal cells.

Binuclear paramagnetic sulfur-nitrosyl iron complexes with aromatic ligands of μ-N—C—S type [N. A. Sanina, S. M. Aldoshin, Funktsional'niye modeli nitrozil'nykh [Fe—S] proteinov ("Functional models of nitrosyl [Fe—S] proteins")// Izv. AN. Ser. Khim. (News of the Academy of Sciences, the Chemical series) (2004), 11, 2326-2345; N. A. Sanina, S. M. Aldoshin, T. N. Rudneva, N. I. Golovina, G. V. Shylov, Yu. M. Shul'ga, V. M. Martynenko, N. S. Ovanesyan, "Sintez, structura I tverdofazniye prevrascheniya nitrizil'nogo complexa zheleza $Na_2[Fe_2(S_2O_3)_2(NO)_4].4H_2O$" ("Synthesis, structure and solid phase conversions of nitrosyl iron complex $Na_2[Fe_2(S_2O_3)_2(NO)_4].4H_2O$"), Koordinatsionnaya Khimiya (Coordination Chemistry), 2005, 31, 301-306; N. A. Sanina, T. N. Rudneva, S. M. Aldoshin, G. V. Shylov, D. V. Korchagin, Yu. M. Shul'ga, V. M. Martynenko, N. S. Ovanesyan, "Influence of $CH_3$ group in 1-methyl-imidazole-2-yl on the properties of binuclear sulfur-nitrosyl iron complex with the ligand of μ-N—C—S type"// Inorganica Chimica Acta (2006), 359, 2, 570-576; N. A. Sanina, T. N. Rudneva, S. M. Aldoshin, A. N. Chekhlov, R. B. Morgunov, E. V. Kurganova, N. S. Ovanesyan, "Sintez, stroeniye i NO-donornaya activnosty paramagnitnogo complexa $[Fe_2(SC_3H_5N_2)_2(NO)_4]$ kak modeli nitrozil'nykh [2Fe-2S] belkov" (Synthesis, structure and NO-donor activity of the paramagnetic complex $[Fe_2(SC_3H_5N_2)_2(NO)_4]$ as a model of nitrosyl [2Fe-2S] proteins"// Izvestiya Akademii nauk. Seriya khimicheskaya (News of the Academy of Sciences, the Chemical series), 1 (2007) 28-34; A. F. Vanin. N. A. Sanina, V. A. Serezhenkov, D. Sh. Burbaev, V. I. Lozinsky and S. M. Aldoshin, Nitric oxide: biology & chemistry 2007, 16, 82-93] which spontaneously generate NO in protonic media are also known, and they have been shown by the recent studies to be useful as highly efficient NO donors in chemotherapy [N. A. Sanina, O. S. Zhukova, Z. S. Smirnova, T. N. Rudneva, G. V. Shylov, S. M. Aldoshin "Biyademiye nitrrozil'niye complexy zheleza s benzagetercyclicheskimi proizvodnymi, sposob ikh polucheniya, donor monooxida azota, pharmacevticheskaya kompozitsiya soderzhashchaya ikh I ikh primeneniye v kachestve protivoopukholevykh lekarstvennykh sredstv" (Binuclear nitrosyl iron complexes with benzazaheterocyclic derivatives, a method for preparing the same, a nitric oxide donor, a pharmaceutical composition comprising the same, and use thereof as anticancer agents)—the application No PCT/RU2007/000286 of 30 May 2007; N. A. Sanina, O. S. Zhukova, S. M. Aldoshin, N. S. Emel'anova, G. K. Gerasimova, "Primenenie tetranitrozil'nogo complexa zheleza s tiophenolom v kachestve protivoopukholevogo lekarstvennogo sredstva i pharmacevticheskiye kompozitsii i nabory soderzhashchiye etot complex" ("Use of tetranitrosyl iron complex with thiophenol as an anticancer agent, and pharmaceutical compositions and kits comprising this complex")—the application No PCT/RU2007000285 of 30 May 2007]. Their wide clinical use, however, is restrained by their low solubility in water and normal saline solution. Thus, there is need in water-soluble (and thus more bioavailable) anticancer agents with enhanced efficacy and lowered toxicity. In the article [S. A. T. Dillinger, H. W. Schmalle, T. Fox, H. Berke, "Developing iron nitrosyl complexes as NO donor prodrugs"// Dalton Trans., (2007)3562-3571] syntheses of binuclear cationic nitrosyl iron complexes with cystamine having the formula $[Fe(NO)_2S(CH_2)_2NH_3]_2X_2$ (X=Cl, I); performing reactions in toxic tetrahydrofuran using iron dinitrosyls $(Fe(CO)_2(NO)_2$ or $\{Fe(NO)_2I\}_2)$ preparable in a multi-step process is required to prepare the main products.

The object of the instant invention is to expand the arsenal of anticancer agents and develop nitrosyl iron complexes-based anticancer agents with improved activity spectrum and decreased side effects, in particular, water-soluble binuclear nitrosyl iron complexes with sulfur-containing aliphatic ligands of natural origin (preferably cystamine, penicillamine) acting as NO-donors and possessing enhanced activity and lowered toxicity.

SUMMARY OF THE INVENTION

In one aspect the invention relates to new water-soluble binuclear cationic nitrosyl iron complexes of formula $[Fe_2(SR)_2(NO)_4]SO_4$,
wherein R is sulfur-containing aliphatic ligands of natural origin such as cystamine, penicillamine, cysteine, S-sulfanylcysteine, different cysteine sulfo-acids, N-acetyl-DL-penicillamine, N-acetylcysteine, thioglycolic acid, mercaptosuccinic acid, methionine, methioninesulfoxide, methioninesulfone, S-adenosylmethionine, glutathione etc. R is preferably cystamine or penicillamine.

In other aspect the invention relates to a method for the preparation of water-soluble binuclear cationic nitrosyl iron complexes with sulfur-containing aliphatic ligands of natural origin of formula $[Fe_2(SR)_2(NO)_4]SO_4$, by treatment of aqueous solution of iron sulfate (II) with respective water-soluble thiol-amine in a stoichiometric ratio in the presence of gaseous NO in acidic medium. This method makes it possible for the first time to prepare the claimed complexes in crystalline form. In an additional aspect, the present invention relates to a donor of nitrogen monoxide, which is the binuclear nitrosyl iron complex with water-soluble sulfur-containing aliphatic ligands characterized above.

In the next aspect, the invention relates to an apoptosis inducer of cancer cells which is the binuclear nitrosyl iron complex with water-soluble sulfur-containing aliphatic ligands characterized above.

In the next aspect, the present invention relates to the use of binuclear nitrosyl iron complexes with sulfur-containing aliphatic ligands of natural origin of formula $[Fe_2(SR)_2(NO)_4]SO_4$, as an anticancer agent.

In an additional aspect, the present invention relates to the use of binuclear nitrosyl iron complexes with sulfur-containing aliphatic ligands of natural origin of formula $[Fe_2(SR)_2(NO)_4]SO_4$, for manufacturing anticancer medicaments.

In the next aspect, the present invention relates to a pharmaceutical composition comprising an efficient amount of a binuclear nitrosyl iron complex with sulfur-containing aliphatic ligands of natural origin of formula $[Fe_2(SR)_2(NO)_4]SO_4$, and a pharmaceutically acceptable carrier.

In the next aspect, the present invention relates to a kit applicable for treating cancer diseases and comprising (1) a pharmaceutical composition comprising a binuclear nitrosyl iron complex with sulfur-containing aliphatic ligands of natural origin of formula $[Fe_2(SR)_2(NO)_4]SO_4$, wherein R has the above-indicated meanings, in a sealed package, and (2) auxiliary agents.

DETAILED DISCLOSURE OF THE INVENTION

According to the present invention, novel binuclear cationic nitrosyl iron complexes with water-soluble thiolyls have a general formula $[Fe_2(SR)_2(NO)_4]SO_4$, wherein R is sulfur-containing aliphatic ligands of natural origin such as cystamine, penicillamine, cysteine, S-sulfanylcysteine, different cysteine sulfo-acids, N-acetyl-DL-penicillamine, N-acetylcysteine, thioglycolic acid, mercaptosuccinic acid, methionine, methioninesulfoxide, methioninesulfone, S-adenosylmethionine, glutathione etc. R is preferably cystamine or penicillamine.

Information about the claimed compounds and a method for preparing the same is lacking in the prior art.

A method for the preparation of binuclear cationic nitrosyl iron complexes with sulfur-containing aliphatic ligands of natural origin of formula $[Fe_2(SR)_2(NO)_4]SO_4$, wherein R has the above-indicated meanings, consists in that aqueous solution of iron sulfate (II) is treated with respective water-soluble thiol-amine in a stoichiometric ratio in the presence of gaseous NO, and the process is carried out in an acidic medium with the subsequent isolation of the target product using the known operations.

The process is preferably carried out at room temperature, advantageously at 18 to 25° C.

The process is preferably carried out in an oxygen-free atmosphere.

Aliphatic amines of natural origin cystamine or penicillamine are preferably used as a water-soluble thiol-amine.

The inventors of the invention have established that binuclear nitrosyl iron complex with sulfur-containing aliphatic ligands of natural origin of the subject invention are effective NO donors, releasing nitrogen monoxide spontaneously upon degradation in proton medium (such as water, blood and components thereof, physiological solutions, etc.) in the absence of chemo-, photo- or enzymatic activation. Thus the complexes of the present invention are a new promising class of nitrogen monoxide donors—synthetic analogues of active sites of nitrosyl non-hemo iron-sulfur proteins—natural NO depot. Therefore, the instant invention in an additional aspect relates to nitrogen monoxide donors, which are binuclear nitrosyl iron complexes with water-soluble ligands of natural origin presented above. Binuclear nitrosyl iron complexes with ligands of natural origin of the present invention exhibit anticancer activity against human The inventors have also established that binuclear nitrosyl iron complexes with ligands of natural origin of the present invention have apoptotic activity with regard to cancer cells. Therefore the present invention in an additional aspect relates to apoptosis inducer of cancer cells which is the binuclear nitrosyl iron complex with water-soluble ligands of natural origin presented above.

The present invention is further directed to the use of binuclear nitrosyl iron complexes of formula $[Fe_2(SR)_2(NO)_4]SO_4$, wherein R has the above-indicated meanings as an anticancer agent. In particular, the compounds of the present invention may be used to treat human line K562 erythroblastic leukemia, ovarian cancer, Ca-755 breast adenocarcinoma, p-388 lymphatic leukemia, B-16 melanoma, Lewis epidermal carcinoma. Iron complexes in accordance with the invention are suitable for inhibiting growth of cancer cells in mammals and they are preferably administered in the form of a pharmaceutical composition comprising an effective amount of the compound according to the present invention in a combination with at least one pharmaceutically or pharmacologically acceptable carrier and/or excipient. The Carrier, also known from the prior art as an excipient, filler, auxiliary substance, additive or diluent, is any substance, which is pharmaceutically inert, imparts respective consistence or form to the composition and does not weaken the therapeutic efficacy of anticancer compounds. The carrier is "pharmaceutically or pharmacologically acceptable" if it does not cause an adverse, allergic or other unfavorable reaction upon the administration to a mammal or human, respectively.

The present invention additionally provides pharmaceutical compositions comprising an effective amount of binuclear nitrosyl iron complex with water-soluble ligands of natural origin of formula $[Fe_2(SR)_2(NO)_4]SO_4$, wherein R has the above-indicated meanings.

A proton-containing medium is preferably used as a pharmaceutically acceptable carrier in the composition of the invention.

Water, normal saline solution or water-soluble biopolymers are preferably used as the proton-containing medium.

Binuclear nitrosyl iron complex with water-soluble ligands of natural origin is present in the composition in an amount of 50 to 100 μM.

Pharmaceutical compositions comprising anticancer compounds according to the present invention may be prepared by any conventional method. The necessary preparative form is selected depending on the selected method of administration. Compositions in accordance with the invention may be produced for any method of administration as long as the target tissue is available via that route of administration. Suitable routes of administration include, but are not limited to, oral, parenteral (e.g., intravenous, intraarterial, subcutaneous, rectal, intramuscular, intraorbital, intracapsular, intraspinal, intraperitoneal, or intrasternal), topical (nasal, transdermal, intraocular), intravesical, intrathecal, into the small intestine, pulmonary, intralymphatic, intracavital, vaginal, transurethral, intradermal, aural, intramammary, buccal, orthotopic, intratracheal, intralesional, percutaneous, endoscopical, transmucosal, sublingual and intestinal administration.

Pharmaceutically acceptable carriers for employing in compositions according to the instant invention are well known to a person skilled in the art, and they are selected depending on a number of factors: a particular anticancer compound being used and concentration, stability and expected bioavailability thereof; human disease, disorder or condition being treated with the composition; subject and his or her age, weight and general condition; and a method of administration. Suitable carriers are readily determinable by a person skilled in the art [J. G. Nairn in: Remington's Pharmaceutical Science (A. Gennaro, ed.), Mack Publishing Co., Easton, Pa., 1985, pp. 1492-1517].

Compositions are preferably prepared in the form of tablets, dispersible powders, pellets, capsules, gelatin capsules, coated caplets, gels, liposomes, granules, solutions, suspensions, emulsions, syrups, elixirs, pastilles, dragee, lozenges or any other dosage form which may be administered orally. The compositions according to the present invention for oral administration comprise an effective amount of the compound according to the invention in a pharmaceutically acceptable carrier. Suitable carriers for solid dosage forms include sugars, starches and other conventional substances including lactose, talc, sucrose, gelatin, carboxymethyl cellulose, agar, mannitol, sorbitol, calcium phosphate, calcium carbonate, sodium carbonate, kaolin, alginic acid, acacia, corn starch, potato starch, sodium saccharinate, magnesium carbonate, tragacanth, microcrystalline cellulose, colloidal silica, sodium crosscarmelose, talc, magnesium stearate and stearic acid. Subsequently, such solid dosage forms can be uncoated or can be coated using the known coating methods for example to delay degradation and absorption. The anticancer compounds of the present invention are also preferably used to prepare a dosage form for parenteral administration for example as a dosage form for injection by intravenous, intraarterial, subcutaneous, rectal, intramuscular, intraorbital, intracapsular, intraspinal, intraperitoneal or intrasternal routes. The compositions of the invention for parenteral administration include an effective amount of an anticancer compound in a pharmaceutically acceptable carrier. Dosage forms suitable for parenteral administration include solutions, suspensions, dispersions, emulsions or any other dosage form, which can be administered parenterally. Techniques and compositions for preparing parenteral dosage forms are known from prior art An insignificant amount of additional components that are well-known in the pharmaceutical industry may be included into compositions of the invention for various purposes. These components to a high degree provide properties which increase the time of retention of the anticancer compound at the site of administration, promote stability of the composition, provide control of the pH, facilitate the introduction of the anticancer compound into the pharmaceutical compositions, and the like. These components each are individually present in an amount preferably less than about 15% by weight, more preferably, less than about 5% by weight and most preferably less than about 0.5% by weight as calculated per a total weight of the composition. Some components such as fillers and diluents can constitute up to 90 weight % of the total weight of the composition, as is well-known in the technology of producing medicinal agents. Such additives include cryoprotective components to prevent precipitation of the iron complex, surfactants, wetting or emulsifying agents (such as for example lecithin, polysorbat-80, Tween® 80, pluronic-60, polyoxyethylene stearate), preservatives (such as for example ethyl-p-hydroxybenzoate), agents preserving from exposure to microbes (such as for example benzyl alcohol, phenol, m-cresol, chlorobutanol, sorbic acid, timerosal and paraben), colorants, dyes, flow aids, non-volatile silicones (e.g., cyclomethicone), agents for adjusting pH value or buffering agents (such as for example acids, bases, sodium acetate, sorbitan monolaurate), components for controlling osmolarity (such as for example glycerol), thickeners (such as for example aluminum monostearate, stearic acid, cetyl alcohol, stearyl alcohol, guar gum, methyl cellulose, hydroxypropyl cellulose, tristearin, cetyl wax esters, polyethylene glycol), colorants, dyes, flow aids, non-volatile silicons (such as for example cyclomethicone, clays (such as for example bentonites), adhesives, bulking agents, flavorings, sweeteners, adsorbents, fillers (such as for example water, saline, electrolyte solutions), binders (such as for example starches such as maize starch, wheat starch, rice starch or potato starch, gelatin, tragacanth, methyl cellulose, hydroxypropyl methyl cellulose, sodium carboxymethyl cellulose, polyvinylpyrrolidone, sugars, polymers, acacia), disintegrating agents (as for example starches such as maize starch, wheat starch, rice starch or potato starch, or carboxymethyl starch, structurated polyvinyl pyrrolidone, agar, alginic acid or a salt thereof, such as sodium alginate, sodium crosscarmelose or crosspovidone), lubricants (such as for example silica talc, stearic acid or salts thereof such as magnesium stearate, or polyethylene glycol), coating agents (such as for example concentrated sugar solutions, including gum arabic, talc, polyvinyl pyrrolidone, carbopol gel, polyethylene glycol, or titanium dioxide) and antioxidants (such as for example sodium meta-bisulfite, sodium bisulfite, sodium sulfite, dextrose, phenols and thiophenols).

Also preferable is that anticancer compounds would have an $ID_{100}$ value (that is, the concentration of the agent causing 100% inhibition of colony formation), at least four-fold less than that of cisplatin when measured according to the technique disclosed in ["Experimental'naya otsenka protivoopukholevykh preparatov v SSSR i SShA" (Experimental assessment of antitumor drugs in the USSR and the USA) Edited by Z. P. Sof'ina, A. B. Syrkina (USSR), A. Goldin, A. Cline (USA) Moscow: "Meditsina" publishing house, 1979, pp. 71-105].

Administration of a dosage form via the indicated routes may be continuous or intermittent, depending, for example, on physiological condition of patients, on the fact whether administration purpose is therapeutic or prophylactic, and on other factors that are known or appreciated by an attending physician.

Doses and administration schedules of pharmaceutical compositions of the invention can be readily determined by an oncologist. It is understood that the dosage of the anticancer compounds depends on the age, sex, health and weight of the recipient, the kind of concurrent treatment, if any, frequency of treatment and the nature of the desired effect. For any mode of administration, the exact amount of the anticancer compound used as well as the prescribed dose needed to achieve beneficial effects disclosed herein, is also in particular dependent on such factors as the bioavailability of the anticancer compound, the human disease being treated, the desired therapeutic dose and other factors that are obvious to one skilled in the art.

The concentration of the anticancer compound in a liquid pharmaceutical composition is, most preferably, 50 to 100 µM. As a rule, relatively low concentrations are preferable, since the anticancer compound is most soluble at low concentrations.

Solutions for parenteral administration can be prepared by dissolving an anticancer compound in water and other proton-containing media (saline solutions, sugar solutions, water-soluble polymers, proteins, electrolyte solutions) for parenteral administration to a patient.

Thus for example, water, saline solutions, dextrose solutions (for example DW5), electrolyte solutions or any other proton, pharmaceutically acceptable medium is typically used for liquid preparative forms.

Proton-containing media such as water, saline solutions, water-soluble polymers, proteins, dextrose solutions (for example DW5), solutions of electrolyte or alcohols from the "PAA Laboratory's" catalogue (2006), p. 26, are preferably useful as the pharmaceutically acceptable carrier in the present invention.

In the next aspect, the present invention relates to a kit for treating cancer diseases which comprises (1) a pharmaceutical composition comprising a binuclear nitrosyl iron complex with sulfur-comprising aliphatic ligands of natural origin of the present invention in a sealed package, and (2) auxiliary agents.

The kit may comprise the composition in the form of a single dosage unit or in the form of multiple doses. The kit may contain forms for oral or parenteral administration.

The pharmaceutical composition in the kit may be filled into glass or polymer vials, ampoules, flasks, dosage cartridges for injectors, blisters, capsules, small packages containing the composition, applicable for oral or parenteral form respectively.

The auxiliary agents comprise liquids for reconstituting the parenterally administrable composition as it is presented in the kit in a concentrated form, for example, in the form of a dry substance, a dried preparation etc.; agents for preparing oral liquid forms and forms for injections ex tempore. Water for injection, normal saline solution, lidocaine solution, and etc. may be used as a liquid for reconstitution. A glucose solution, solution of sugars, syrups etc. may be used to reconstitute a composition used orally in a liquid form. Optional auxiliary agents of the kit include means for opening seals, means for sealing opened reusable seals, instruction inserts.

A pharmaceutical composition that is a solid dosage form for oral administration may be presented in the kit in the form of tablets, capsules in blisters, ampoules, flasks, vials, small packets etc. A pharmaceutical composition that is a liquid dosage form for parenteral or oral administration may be presented in the kit in flasks, capsules, ampoules, cartridges etc.

An example of a kit for parenteral administration includes a package wherein instruction for use, ampoules or flasks with a dry composition and ampoules with normal saline solution for injections are arranged. A device for opening ampoules is arranged in the package. Ampoules are packed into blisters each containing 10 ampoules.

Other variants of the kit are obvious to one skilled in the art in this field from the description presented above.

The following examples are provided only as an additional illustration of the invention and they should not be given consideration as limitation of the invention.

SYNTHESIS EXAMPLES OF THE COMPLEXES

Example 1

Di-µ-cystamine tetranitrosyl di-iron sulphate ($Fe_2S_3N_6C_4H_{19}O_{10.5}$) (I) was prepared by reacting iron sulphate (II) with cystamine hydrochloride solution. Distilled water used in the synthesis required preliminary preparation to remove oxygen dissolved therein. To this end, a flow of inert gas (argon or nitrogen) was passed through a flask with distilled water for 30 minutes. 0.84 grams (3 mmol) iron sulphate heptahydrate were dissolved in 12 ml prepared distilled water. To this solution, 0.40 g (3.5 mmol) cystamine hydrochloride dissolved in 8 ml water was added to this solution. Nitrogen monoxide flow prepared according to the technique [Yu. V. Karyakin and I. I. Angeov. Chistiye khimicheskiye veshchestva (Pure chemical substances), Moscow: Khimiya publishing house, 1974, 23] was passed through the prepared solution for 1 to 1.5 hours at ~40° C. until crystals were formed in the solution. Reaction mixture was then allowed to stand at 6 to 8° C. for 15 to 20 hrs; a formed brown-red fine crystalline precipitate was filtered off and dried in air for 24 hours. Yield was 0.1443 mg (16.5%). The complex was readily soluble in water and DMSO, it was less soluble in methanol, it was insoluble in other organic solvents (ethanol, THF, heptanes, acetonitryl, ether etc.). Polycrystals of this complex are rather stable and remain stable in air at room temperature for a rather long time.

Found, %: Fe, 21.57; S, 18.39; N, 16.34; C, 9.40; H, 2.38.

Calculated, %: Fe=21.58; S=18.50; N=16.18; C=9.25; O=32.37; H=2.12.

IR-spectrum (in KBr tablets), (cm$^{-1}$): 3,454 (medium), 3,003 (weak), 2,927 (weak), 1,769 (strong), 1,727 (strong), 1,461 (weak), 1,385 (medium), 1,340 (medium), 1,266 (medium), 1,120 (strong), 770 (weak), 620 (strong). $V_{NO}$: 1,769 and 1,727 cm$^{-1}$.

Example 2

Di-µ-penicillamine-tetranitrosyl di-iron sulphate ($Fe_2S_3N_6C_{10}H_{32}O_{17}$) (II) was prepared by reacting iron sulphate (II) with D-penicillamine in a ratio 1:3. The reaction was carried out using a standard vacuum line and Shlenk's technology under nitrogen at room temperature. Oxygen was preliminary removed from water using the method of triplicate freezing and pumping off under vacuum. To a dry mixture comprising 0.42 g (1.5 mmol) iron sulphate heptahydrate and 0.68 g (4.5 mmol) D-penicillamine, 10 ml prepared water were added. Nitrogen monoxide produced according to the known technique [Yu. V. Karyakin and I. I. Angelov. Chistiye khimicheskiye veshchestva (Pure chemical substances), Moscow: Khimiya publishing house, 1974, 23] was passed through the dark-violet solution formed. During the reaction, the solution attained dark-red color. Small spicular red crystals gradually filling all the solution volume were appearing in 10 to 12 minutes on the reaction vessel walls. They were filtered under vacuum and dried under argon. Yield was: 98 mg (11.3%). The product obtained was stable in the absence of inert atmosphere for a long time. The remaining stock solution was allowed to stand for another three days at temperature 6 to 8° C. Red-orange spicular crystals thus obtained were suitable for X-ray diffraction analysis (XRD).

Found, %: Fe, 15.62; S, 13.34; N, 11.89; C, 16.80, H, 4.62.

Calculated, %: Fe=15.64; S=13.42; N=11.72; C=16.76, O=37.99; H=4.47.

IR-spectrum (in KBr tablets), (cm$^{-1}$): 1771 (strong), 1723 (strong), 1626 (medium), 1375 (medium), 1337 (medium), 1269 (medium), 1189 (medium), 1114 (medium), 1089 (medium), 746 (medium). $v_{NO}$: 1771 и1723 cm$^{-1}$.

X-ray diffraction analysis of the complexes I and II was carried out on the SMART APEX2 CCD (Bruker) diffractometer [λ(MoKα)=0.71072 Å, ω-scans, 2θ<56°] at 100K.

Crystallographic data and the main parameters of the further definition are presented in Tables 1 and 2. Interatomic distances and angles are presented in Tables 3 and 4. Crystallochemical parameters were deposited in the Cambridge Crystallographic data Bank (CCDC for I-663194, for II-680286).

TABLE 1

Crystallographic data and characteristics of analysis for the complex I

| Empirical formula | $C_4H_{19}Fe_2N_6O_{10.50}S_3$ |
| --- | --- |
| Molecular weight | 527.13 |
| Temperature | 100(2) K. |
| Wavelength | 0.71073 Å |
| Crystal system, space group | Triclinic, P-1 |
| a | 6.8503(11) Å |
| b | 10.5747(16) Å |
| c | 13.723(2) Å |
| alpha | 90.884(3)°, |
| beta | 95.900(3)°, |
| gamma | 90.635(3)°, |
| V | 988.6(3) Å$^3$ |
| Z, $d_{calc}$. | 2; 1.771 mg/m$^3$ |
| µ | 1.839 mm$^{-1}$ |
| F(000) | 538 |
| Crystal size | 0.35 × 0.04 × 0.03 mm$^3$ |
| Theta range for data collection | from 1.93 to 28.00° |
| Reflections collected/unique | 5969 |
| N/number of parameters | |
| GOOF according to F^2 | 0.930 |
| R index for reflections with [I > 2(σ)(I) | R1 = 0.0548, wR2 = 0.1058 |
| R index for all reflections | R1 = 0.1053, wR2 = 0.1204 |

TABLE 2

Crystallographic data and characteristics of analysis for the complex II

| Empirical formula | $C_{10}H_{32}Fe_2N_6O_{17}S_3$ |
| --- | --- |
| Molecular weight | 716.30 |
| Temperature | 100(2) K. |
| Wavelength | 0.71073 Å |
| Crystal system, space group | Monoclinic, P2$_1$ |
| a | 6.1878(4) Å |
| b | 28.2739(17) Å |
| c | 7.8615(5) Å |
| alpha | 90° |
| beta | 102.4557(14)° |
| gamma | 90° |
| V | 1343.02(15) Å$^3$ |
| Z, $d_{calc}$. | 2; 1.771 mg/m$^3$ |
| µ | 1.397 mm$^{-1}$ |
| F(000) | 740 |
| Crystal size | 0.36 × 0.10 × 0.04 mm$^3$ |
| Theta range for data collection | from 2.65 to 28.99° |
| Reflections collected/unique | 6900 |
| N/number of parameters | |
| GOOF according to F^2 | 1.029 |
| R index for reflections with [I > 2(σ)(I) | R1 = 0.0392, wR2 = 0.0811 |
| R index for all reflections | R1 = 0.0491, wR2 = 0.0854 |

TABLE 3

Interatomic distance and valence angles in the structure of complex I

| Bond, | Å | Bond, | Å |
| --- | --- | --- | --- |
| Fe(1)—N(2) | 1.660(5) | Fe(1)—N(1) | 1.675(5) |
| Fe(1)—S(1) | 2.2444(15) | Fe(1)—S(1)#1 | 2.2525(15) |
| Fe(1)—Fe(1)#1 | 2.6725(15) | S(1)—C(1) | 1.837(5) |
| S(1)—Fe(1)#1 | 2.2525(15) | O(1)—N(1) | 1.164(5) |
| O(2)—N(2) | 1.180(5) | N(3)—C(2) | 1.490(6) |
| N(3)—H(3NA) | 1.0315 | N(3)—H(3NC) | 0.8500 |
| N(3)—H(3NB) | 0.8500 | C(1)—C(2) | 1.504(7) |

TABLE 3-continued

Interatomic distance and valence angles in the structure of complex I

| Bond | Å | Bond | Å |
|---|---|---|---|
| C(1)—H(1A) | 0.9900 | C(1)—H(1B) | 0.9900 |
| C(2)—H(2A) | 0.9900 | C(2)—H(2B) | 0.9900 |
| Fe(1')—N(1') | 1.667(4) | Fe(1')—N(2') | 1.668(5) |
| Fe(1')—S(1')#2 | 2.2447(15) | Fe(1')—S(1') | 2.2507(15) |
| Fe(1')—Fe(1')#2 | 2.6823(15) | S(1')—C(1') | 1.826(5) |
| S(1')—Fe(1')#2 | 2.2447(15) | O(1')—N(1') | 1.175(5) |
| O(2')—N(2') | 1.172(5) | N(3')—C(2') | 1.478(6) |
| N(3')—H(3NF) | 0.8500 | N(3')—H(3ND) | 0.8499 |
| N(3')—H(3NE) | 0.9527 | C(1')—C(2') | 1.500(7) |
| C(1')—H(1'A) | 0.9900 | C(1')—H(1'B) | 0.9900 |
| C(2')—H(2'A) | 0.9900 | C(2')—H(2'B) | 0.9900 |
| S(1S)—O(3S) | 1.460(4) | S(1S)—O(2S) | 1.461(4) |
| S(1S)—O(1S) | 1.463(4) | S(1S)—O(4S) | 1.474(4) |
| O(1W)—H(1WB) | 0.8500 | O(1W)—H(1WA) | 0.8499 |
| O(2W)—H(2WA) | 0.8499 | O(2W)—H(2WB) | 0.8500 |
| O(3W)—H(3WB) | 0.8499 | O(3W)—H(3WA) | 0.8500 |

| Valence angle, | ° | Valence angle, | ° |
|---|---|---|---|
| N(2)—Fe(1)—N(1) | 121.6(2) | | |
| N(2)—Fe(1)—S(1) | 106.61(16) | N(1)—Fe(1)—S(1) | 104.59(15) |
| N(2)—Fe(1)—S(1)#1 | 108.03(16) | N(1)—Fe(1)—S(1)#1 | 108.06(15) |
| S(1)—Fe(1)—S(1)#1 | 107.07(5) | N(2)—Fe(1)—Fe(1)#1 | 120.07(16) |
| N(1)—Fe(1)—Fe(1)#1 | 118.22(15) | S(1)—Fe(1)—Fe(1)#1 | 53.68(4) |
| S(1)#1—Fe(1)—Fe(1)#1 | 53.40(4) | C(1)—S(1)—Fe(1) | 106.78(17) |
| C(1)—S(1)—Fe(1)#1 | 108.44(18) | Fe(1)—S(1)—Fe(1)#1 | 72.93(5) |
| O(1)—N(1)—Fe(1) | 171.4(4) | O(2)—N(2)—Fe(1) | 173.7(4) |
| C(2)—N(3)—H(3NA) | 114.5 | C(2)—N(3)—H(3NC) | 111.2 |
| H(3NA)—N(3)—H(3NC) | 109.7 | C(2)—N(3)—H(3NB) | 108.8 |
| H(3NA)—N(3)—H(3NB) | 112.4 | H(3NC)—N(3)—H(3NB) | 99.1 |
| C(2)—C(1)—S(1) | 109.4(4) | C(2)—C(1)—H(1A) | 109.8 |
| S(1)—C(1)—H(1A) | 109.8 | C(2)—C(1)—H(1B) | 109.8 |
| S(1)—C(1)—H(1B) | 109.8 | H(1A)—C(1)—H(1B) | 108.2 |
| N(3)—C(2)—C(1) | 110.0(4) | N(3)—C(2)—H(2A) | 109.7 |
| C(1)—C(2)—H(2A) | 109.7 | N(3)—C(2)—H(2B) | 109.7 |
| C(1)—C(2)—H(2B) | 109.7 | H(2A)—C(2)—H(2B) | 108.2 |
| N(1')—Fe(1')—N(2') | 121.3(2) | N(1')—Fe(1')—S(1')#2 | 103.85(15) |
| N(2')—Fe(1')—S(1')#2 | 107.69(16) | N(1')—Fe(1')—S(1') | 110.10(15) |
| N(2')—Fe(1')—S(1') | 106.37(15) | S(1')#2—Fe(1')—S(1') | 106.74(5) |
| N(1')—Fe(1')—Fe(1')#2 | 119.25(15) | N(2')—Fe(1')—Fe(1')#2 | 119.39(15) |
| S(1')#2—Fe(1')—Fe(1')#2 | 53.47(4) | S(1')—Fe(1')—Fe(1')#2 | 53.27(4) |
| C(1')—S(1')—Fe(1')#2 | 105.82(17) | C(1')—S(1')—Fe(1') | 107.88(18) |
| Fe(1')#2—S(1')—Fe(1') | 73.26(5) | O(1')—N(1')—Fe(1') | 171.2(4) |
| O(2')—N(2')—Fe(1') | 172.4(4) | C(2')—N(3')—H(3NF) | 110.1 |
| C(2')—N(3')—H(3ND) | 110.3 | H(3NF)—N(3')—H(3ND) | 102.8 |
| C(2')—N(3')—H(3NE) | 104.9 | H(3NF)—N(3')—H(3NE) | 111.2 |
| H(3ND)—N(3')—H(3NE) | 117.5 | C(2')—C(1')—S(1') | 110.3(4) |
| C(2')—C(1')—H(1'A) | 109.6 | S(1')—C(1')—H(1'A) | 109.6 |
| C(2')—C(1')—H(1'B) | 109.6 | S(1')—C(1')—H(1'B) | 109.6 |
| H(1'A)—C(1')—H(1'B) | 108.1 | N(3')—C(2')—C(1') | 110.6(4) |
| N(3')—C(2')—H(2'A) | 109.5 | C(1')—C(2')—H(2'A) | 109.5 |
| N(3')—C(2')—H(2'B) | 109.5 | C(1')—C(2')—H(2'B) | 109.5 |
| H(2'A)—C(2')—H(2'B) | 108.1 | O(3S)—S(1S)—O(2S) | 109.4(2) |
| O(3S)—S(1S)—O(1S) | 109.2(2) | O(2S)—S(1S)—O(1S) | 109.7(3) |
| O(3S)—S(1S)—O(4S) | 110.9(2) | O(2S)—S(1S)—O(4S) | 108.8(2) |
| O(1S)—S(1S)—O(4S) | 108.7(2) | H(1WB)—O(1W)—H(1WA) | 99.0 |
| H(2WA)—O(2W)—H(2WB) | 117.2 | H(3WB)—O(3W)—H(3WA) | 95.4 |

The matrixes of generation of equivalent positions of the atoms:
1 – x. – y + 1. –z + 2
2 – x + 1. – y. – z + 2

TABLE 4

Interatomic distance and valence angles in the structure of complex II

| Bond, | Å | Bond, | Å |
|---|---|---|---|
| Fe(1)—N(2) | 1.666(3) | Fe(1)—N(1) | 1.669(3) |
| Fe(1)—S(2) | 2.2545(10) | Fe(1)—S(1) | 2.2620(9) |
| Fe(1)—Fe(2) | 2.7088(6) | Fe(2)—N(4) | 1.676(3) |
| Fe(2)—N(3) | 1.680(3) | Fe(2)—S(2) | 2.2564(9) |
| Fe(2)—S(1) | 2.2601(11) | S(1)—C(1) | 1.873(3) |
| S(2)—C(6) | 1.868(4) | N(1)—O(1) | 1.170(4) |
| N(2)—O(2) | 1.172(4) | N(3)—O(3) | 1.162(4) |
| N(4)—O(4) | 1.165(4) | N(5)—C(2) | 1.496(5) |

TABLE 4-continued

Interatomic distance and valence angles in the structure of complex II

| | | | |
|---|---|---|---|
| N(5)—H(5NC) | 0.8500 | N(5)—H(5NB) | 0.8500 |
| N(5)—H(5NA) | 0.8498 | O(5)—C(3) | 1.216(4) |
| O(6)—C(3) | 1.304(4) | O(6)—H(6O) | 0.8500 |
| N(6)—C(7) | 1.489(5) | N(6)—H(6NC) | 0.8500 |
| N(6)—H(6NB) | 0.8500 | N(6)—H(6NA) | 0.8499 |
| O(7)—C(8) | 1.198(4) | O(8)—C(8) | 1.322(4) |
| O(8)—H(8O) | 0.8501 | C(1)—C(5) | 1.530(5) |
| C(1)—C(4) | 1.541(5) | C(1)—C(2) | 1.554(5) |
| C(2)—C(3) | 1.529(5) | C(2)—H(2A) | 1.0000 |
| C(4)—H(4A) | 0.9800 | C(4)—H(4B) | 0.9800 |
| C(4)—H(4C) | 0.9800 | C(5)—H(5A) | 0.9800 |
| C(5)—H(5B) | 0.9800 | C(5)—H(5C) | 0.9800 |
| C(6)—C(10) | 1.512(5) | C(6)—C(9) | 1.538(5) |
| C(6)—C(7) | 1.557(5) | C(7)—C(8) | 1.531(5) |
| C(7)—H(7A) | 1.0000 | C(9)—H(9A) | 0.9800 |
| C(9)—H(9B) | 0.9800 | C(9)—H(9C) | 0.9800 |
| C(10)—H(10A) | 0.9800 | C(10)—H(10B) | 0.9800 |
| C(10)—H(10C) | 0.9800 | O(1W)—H(1WB) | 0.8500 |
| O(1W)—H(1WA) | 0.8500 | O(1S)—S(3') | 1.455(5) |
| O(1S)—S(3) | 1.492(5) | S(3)—O(4S) | 1.481(3) |
| S(3)—O(3S) | 1.482(3) | S(3)—O(2S) | 1.486(3) |
| S(3')—O(3S') | 1.481(3) | S(3')—O(4S') | 1.481(3) |
| S(3')—O(2S') | 1.483(3) | O(2W)—H(2WB) | 0.8501 |
| O(2W)—H(2WA) | 0.8501 | O(3W)—H(3WB) | 0.8500 |
| O(3W)—H(3WA) | 0.8500 | O(4W)—H(4WB) | 0.8500 |
| O(4W)—H(4WA) | 0.8500 | | |

| Valence angle, | ° | Valence angle, | ° |
|---|---|---|---|
| N(2)—Fe(1)—N(1) | 113.95(14) | N(2)—Fe(1)—S(2) | 111.94(11) |
| N(1)—Fe(1)—S(2) | 106.21(10) | N(2)—Fe(1)—S(1) | 106.47(11) |
| N(1)—Fe(1)—S(1) | 111.79(10) | S(2)—Fe(1)—S(1) | 106.29(4) |
| N(2)—Fe(1)—Fe(2) | 122.38(10) | N(1)—Fe(1)—Fe(2) | 123.67(10) |
| S(2)—Fe(1)—Fe(2) | 53.13(2) | S(1)—Fe(1)—Fe(2) | 53.17(3) |
| N(4)—Fe(2)—N(3) | 113.40(14) | N(4)—Fe(2)—S(2) | 111.37(11) |
| N(3)—Fe(2)—S(2) | 104.79(11) | N(4)—Fe(2)—S(1) | 108.57(11) |
| N(3)—Fe(2)—S(1) | 112.19(11) | S(2)—Fe(2)—S(1) | 106.29(4) |
| N(4)—Fe(2)—Fe(1) | 123.85(10) | N(3)—Fe(2)—Fe(1) | 122.68(10) |
| S(2)—Fe(2)—Fe(1) | 53.06(3) | S(1)—Fe(2)—Fe(1) | 53.23(3) |
| C(1)—S(1)—Fe(2) | 112.90(12) | C(1)—S(1)—Fe(1) | 116.61(11) |
| Fe(2)—S(1)—Fe(1) | 73.60(3) | C(6)—S(2)—Fe(1) | 114.39(11) |
| C(6)—S(2)—Fe(2) | 116.40(11) | Fe(1)—S(2)—Fe(2) | 73.81(3) |
| O(1)—N(1)—Fe(1) | 165.8(3) | O(2)—N(2)—Fe(1) | 169.8(3) |
| O(3)—N(3)—Fe(2) | 169.1(3) | O(4)—N(4)—Fe(2) | 164.4(3) |
| C(2)—N(5)—H(5NC) | 116.0 | C(2)—N(5)—H(5NB) | 113.8 |
| H(5NC)—N(5)—H(5NB) | 102.7 | C(2)—N(5)—H(5NA) | 109.8 |
| H(5NC)—N(5)—H(5NA) | 105.9 | H(5NB)—N(5)—H(5NA) | 108.1 |
| C(3)—O(6)—H(6O) | 110.8 | C(7)—N(6)—H(6NC) | 109.8 |
| C(7)—N(6)—H(6NB) | 113.5 | H(6NC)—N(6)—H(6NB) | 101.4 |
| C(7)—N(6)—H(6NA) | 102.2 | H(6NC)—N(6)—H(6NA) | 111.0 |
| H(6NB)—N(6)—H(6NA) | 119.0 | C(8)—O(8)—H(8O) | 111.5 |
| C(5)—C(1)—C(4) | 109.5(3) | C(5)—C(1)—C(2) | 110.4(3) |
| C(4)—C(1)—C(2) | 109.5(3) | C(5)—C(1)—S(1) | 114.6(3) |
| C(4)—C(1)—S(1) | 105.3(2) | C(2)—C(1)—S(1) | 107.2(2) |
| N(5)—C(2)—C(3) | 107.7(3) | N(5)—C(2)—C(1) | 110.9(3) |
| C(3)—C(2)—C(1) | 114.7(3) | N(5)—C(2)—H(2A) | 107.8 |
| C(3)—C(2)—H(2A) | 107.8 | C(1)—C(2)—H(2A) | 107.8 |
| O(5)—C(3)—O(6) | 125.2(3) | O(5)—C(3)—C(2) | 122.4(3) |
| O(6)—C(3)—C(2) | 112.4(3) | C(1)—C(4)—H(4A) | 109.5 |
| C(1)—C(4)—H(4B) | 109.5 | H(4A)—C(4)—H(4B) | 109.5 |
| C(1)—C(4)—H(4C) | 109.5 | H(4A)—C(4)—H(4C) | 109.5 |
| H(4B)—C(4)—H(4C) | 109.5 | C(1)—C(5)—H(5A) | 109.5 |
| C(1)—C(5)—H(5B) | 109.5 | H(5A)—C(5)—H(5B) | 109.5 |
| C(1)—C(5)—H(5C) | 109.5 | H(5A)—C(5)—H(5C) | 109.5 |
| H(5B)—C(5)—H(5C) | 109.5 | C(10)—C(6)—C(9) | 109.7(3) |
| C(10)—C(6)—C(7) | 113.9(3) | C(9)—C(6)—C(7) | 109.5(3) |
| C(10)—C(6)—S(2) | 115.0(2) | C(9)—C(6)—S(2) | 105.0(2) |
| C(7)—C(6)—S(2) | 103.2(2) | N(6)—C(7)—C(8) | 109.2(3) |
| N(6)—C(7)—C(6) | 112.8(3) | C(8)—C(7)—C(6) | 113.1(3) |
| N(6)—C(7)—H(7A) | 107.1 | C(8)—C(7)—H(7A) | 107.1 |
| C(6)—C(7)—H(7A) | 107.1 | O(7)—C(8)—O(8) | 125.7(3) |
| O(7)—C(8)—C(7) | 122.6(3) | O(8)—C(8)—C(7) | 111.7(3) |
| C(6)—C(9)—H(9A) | 109.5 | C(6)—C(9)—H(9B) | 109.5 |
| H(9A)—C(9)—H(9B) | 109.5 | C(6)—C(9)—H(9C) | 109.5 |
| H(9A)—C(9)—H(9C) | 109.5 | H(9B)—C(9)—H(9C) | 109.5 |
| C(6)—C(10)—H(10A) | 109.5 | C(6)—C(10)—H(10B) | 109.5 |
| H(10A)—C(10)—H(10B) | 109.5 | C(6)—C(10)—H(10C) | 109.5 |
| H(10A)—C(10)—H(10C) | 109.5 | H(10B)—C(10)—H(10C) | 109.5 |

TABLE 4-continued

| Interatomic distance and valence angles in the structure of complex II | | | |
|---|---|---|---|
| H(1WB)—O(1W)—H(1WA) | 118.4 | O(4S)—S(3)—O(3S) | 109.3(4) |
| O(4S)—S(3)—O(2S) | 113.3(4) | O(3S)—S(3)—O(2S) | 110.0(4) |
| O(4S)—S(3)—O(1S) | 111.1(4) | O(3S)—S(3)—O(1S) | 111.3(4) |
| O(2S)—S(3)—O(1S) | 101.7(3) | O(1S)—S(3')—O(3S') | 106.5(3) |
| O(1S)—S(3')—O(4S') | 112.2(3) | O(3S')—S(3')—O(4S') | 108.1(4) |
| O(1S)—S(3')—O(2S') | 112.6(4) | O(3S')—S(3')—O(2S') | 112.0(4) |
| O(4S')—S(3')—O(2S') | 105.3(4) | H(2WB)—O(2W)—H(2WA) | 114.8 |
| H(3WB)—O(3W)—H(3WA) | 111.4 | H(4WB)—O(4W)—H(4WA) | 97.7 |

Figure 1:
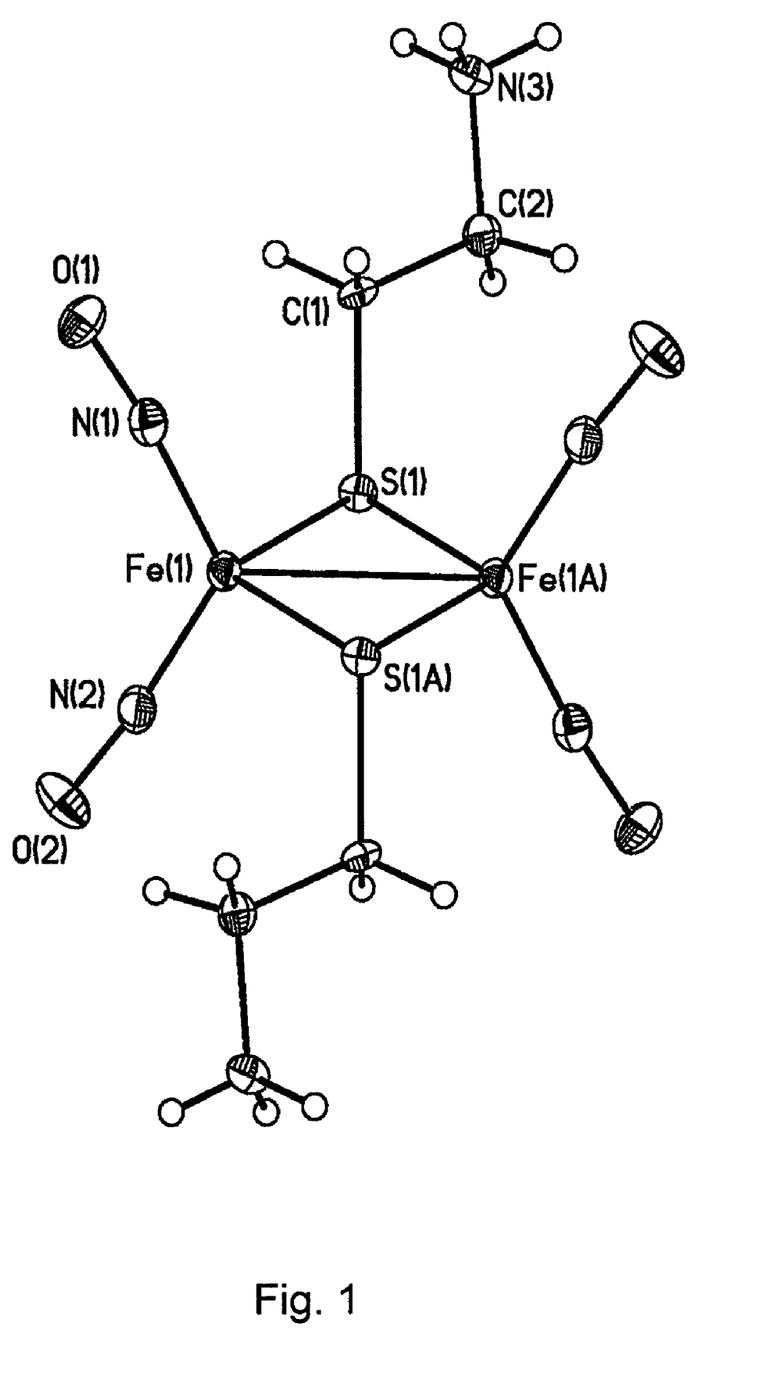
FIG. 1 represents the molecular structure of the complex $[Fe_2(S(CH_2)_2NH_3)_2(NO)_4]SO_4 \cdot 2{,}5H_2O$ (complex I).
Figure 3:
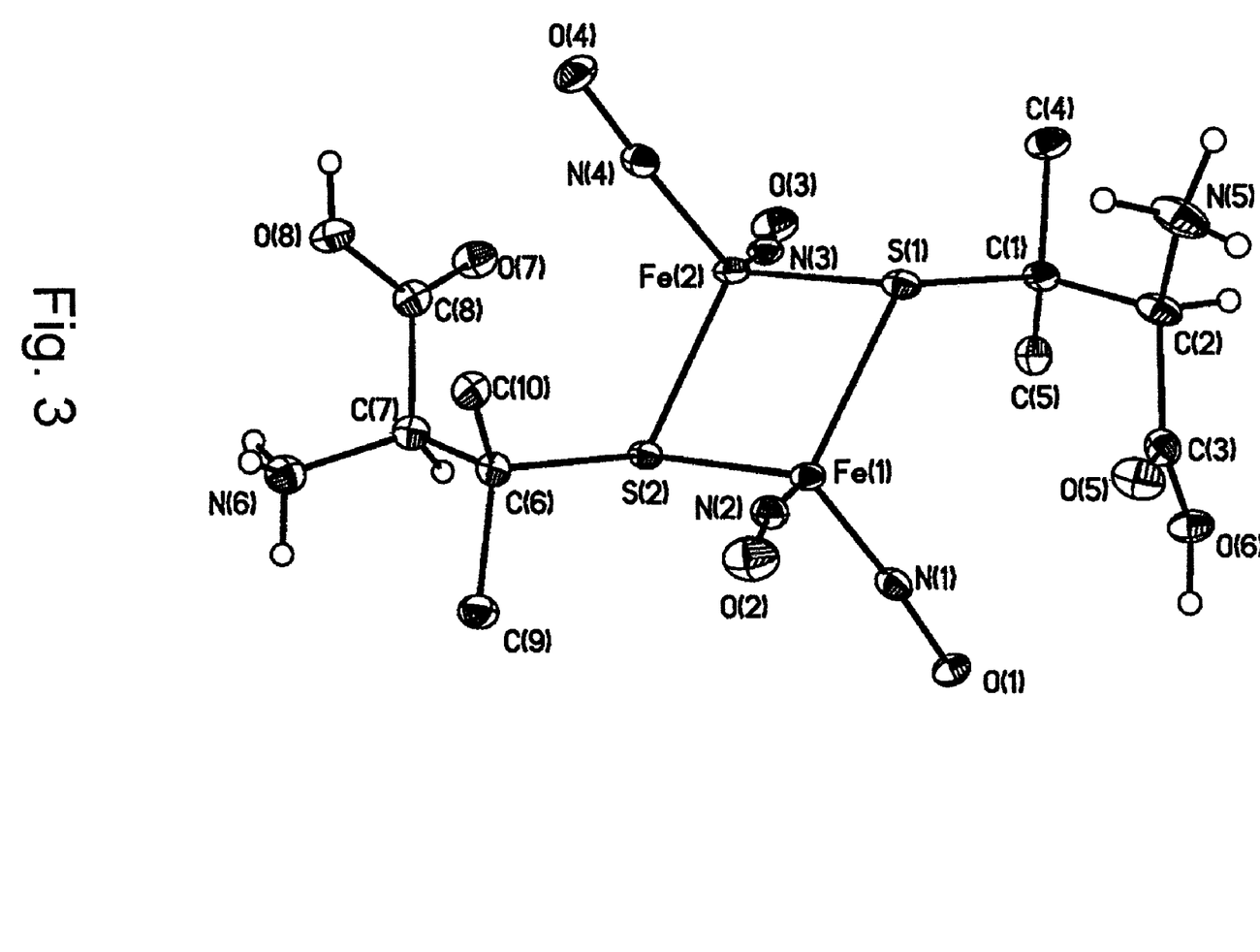
FIG. 3 represents the molecular structure of the complex $[Fe_2(S(C(CH_3)_2CH(NH_3)COOH))_2(NO)_4]SO_4 \cdot 5H_2O$ (complex II).

Molecular structures of the complexes I and II are presented in FIGS. 1 and 3 respectively. According to the data of XRD of I, one molecule of sulfate of dication [Fe$_2$(S(CH$_2$)$_2$NH$_3$)$_2$(NO)$_4$]$^{2+}$ was crystallized with 2.5 molecules of water. In the crystalline structure of I, there are two independent dications (the both are centro symmetric) wherein iron atoms are bound to two nitrogen atoms of nitrosyl ligands and to two atoms of μ-S protonated cystamine ligands. The latter are characterized by antiperiplanar conformation with torsion angles SCCN equal to 169.1 and 179.8°. Iron atoms, except for the bond Fe(1)-Fe(1A) are in a slightly distorted tetrahedral configuration with the maximum angle deviation NO—Fe—NO up to 121.3(2)°. While geometry of the two independent dications is almost identical, the distances Fe . . . Fe therein are somewhat different and they are equal to 2.672 (1) and 2.682 (1) Å. Deviation from linearity of the Fe—NO bonds averaged about 10°. On one hand, this may result from geometry of the four-member ring Fe$_2$S$_2$ only. It must be noted that the distance Fe . . . Fe in such complexes is rather sensitive to the effects of crystalline packing and, for example, in the above-mentioned complex it is equal to 2.715 (1) Å.

There are one sulfate anion and 5 molecules of water per one molecule of dication of complex II. Dication has centrosymmetric dimeric binuclear structure wherein two tetrahedrally coordinated iron atoms are bound to two NO groups and two penicillamine thiols. Iron atoms are bound with each other via the μ-S fragment of penicillamine ligands. The distance Fe(1)-Fe(2) is 2.7088(6).

Summarizing the dication geometry analysis data, one may conclude that the structure of the complexes I and II relates to the structural type of Roussin's red salt esters [N. A. Sanina, S. M. Aldoshin, Izvestiya AN Seriya Khimiya (News of the Academy of Sciences, Chemistry Series), 2004, 11, 2326]. Taking into consideration that the complexes/and II are diamagnetic, the rather small distance Fe . . . Fe can indicate to the presence of a bond between iron atoms.

Figure 2:
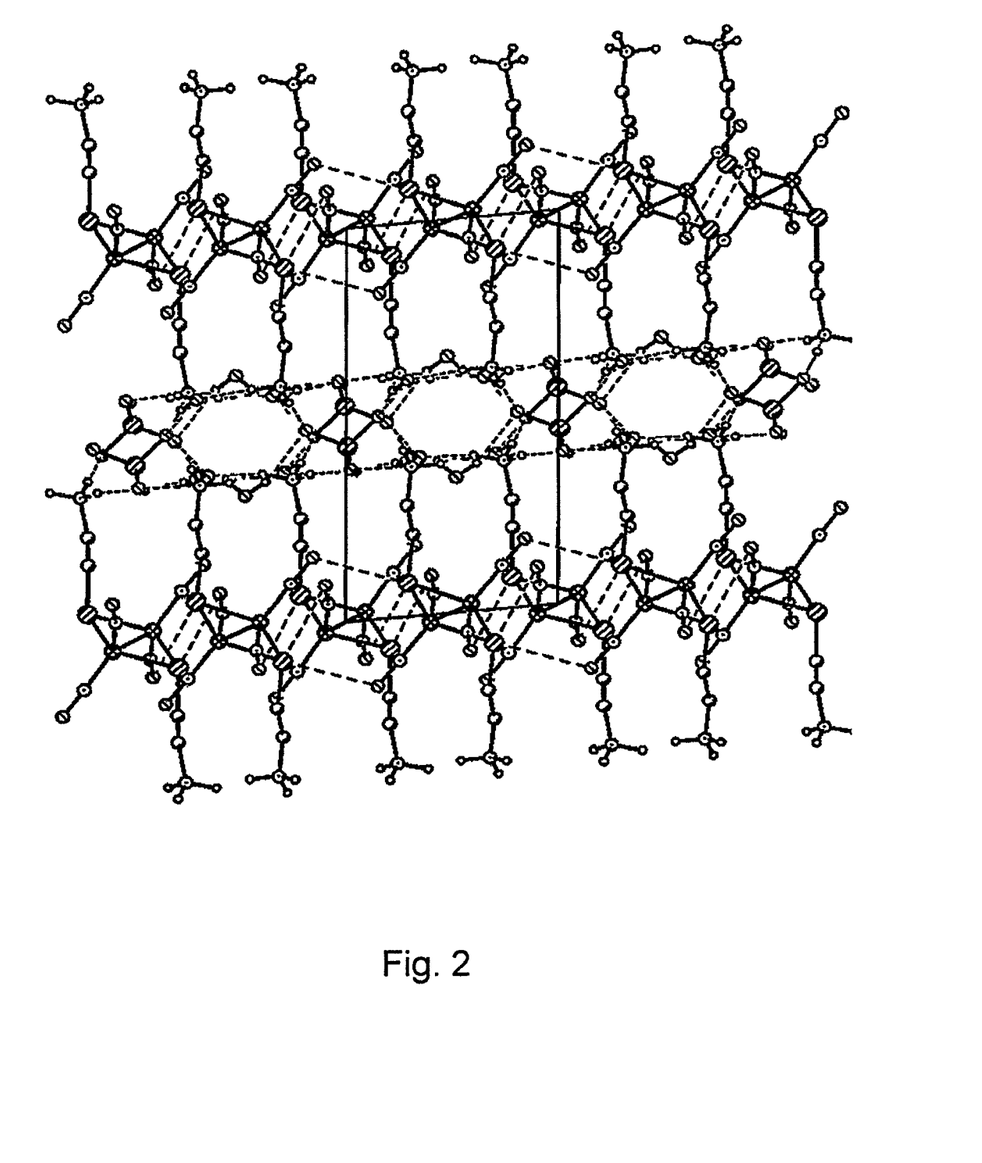
FIG. 2 represents the crystalline structure of the complex I.
Figure 4:
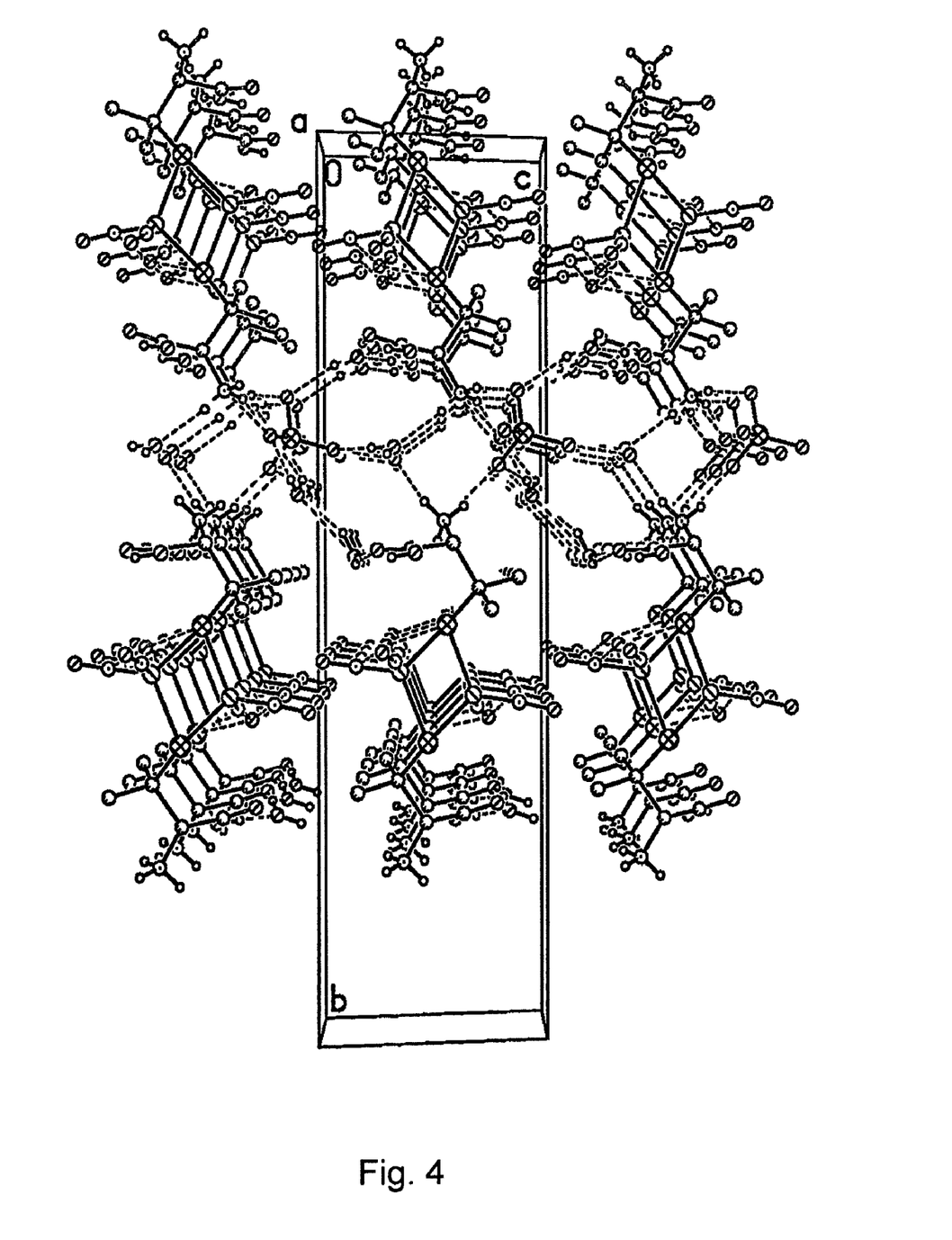
FIG. 4 represents the crystalline structure of the complex II.

Crystalline structures of the complexes I and II are presented in FIGS. 2 and 4 respectively.

Study of NO-donor Activity of the Complexes I and II

The sensor electrode "amiNO-700" of the system "inNO Nitric Oxide Measuring System" (Innovative Instruments, Inc., Tampa, Fla., USA) was used to determine NO generated by the complexes I and II in water. NO concentration was recorded for ~1,600 seconds (with a step of 0.2 seconds) with concentration of NO donor (0.1 μmol). A standard aqueous solution of NaNO$_2$ (100 μmol) to which a mixture of 0.12M KCl and 2 ml 1M H$_2$SO$_4$ in 18 ml water was added was used to calibrate the electrochemical sensor. All the experiments were carried out in aerobic solutions at temperature 25° C. pH of solutions was measured using the membrane pH-meter "HI 8314" (HANNA Instruments, Germany).

Figure 5:
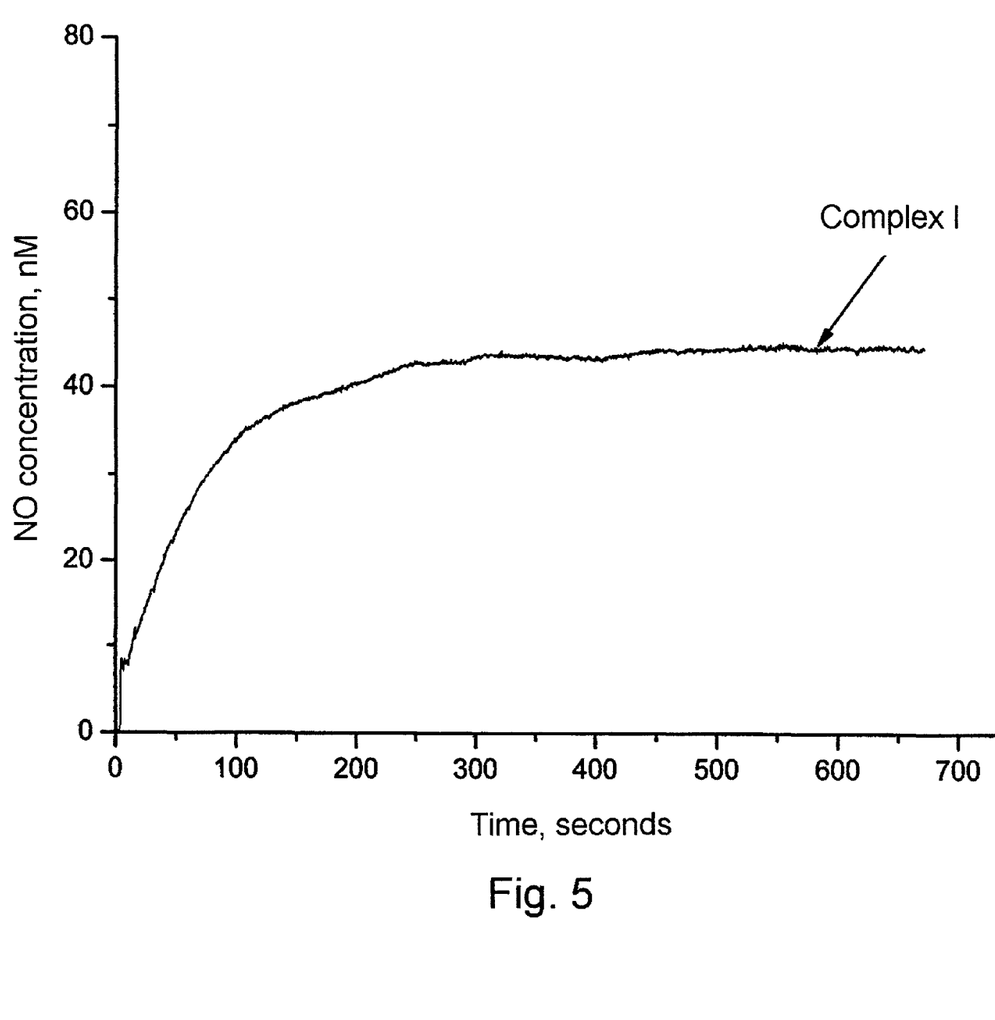
FIGS. 5 and 6 show NO concentration versus time upon degradation of the complexes I and II ($4 \cdot 10^{-6}$ M) in water under anaerobic conditions at pH=6.25 and temperature 25° C.
Figure 6:
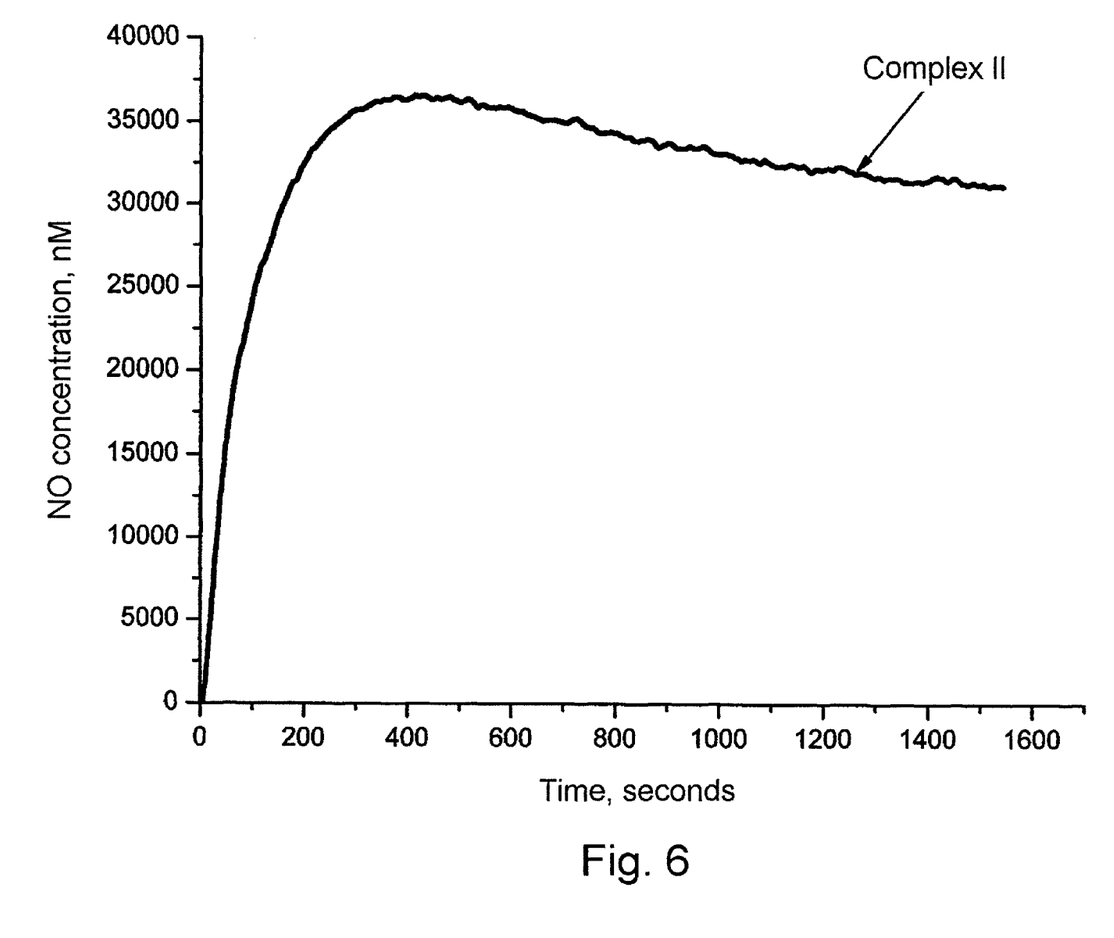

The complexes I and II were established to spontaneously (i.e. in the absence of chemo-, photo- or enzymatic activation, see FIGS. 5 and 6) generate NO in aerobic aqueous solutions. Unlike binuclear nitrosyl iron complexes with aromatic thiolyls, the complexes I and II exhibit prolonged release of NQ.

Cytotoxicity Study of Water-soluble Iron Complexes I and II on Human Cancer Cells in vitro Cells of line K562 human erythroblastic leukemia and A549 non-small cell lung cancer were used as the study object. The cells were grown in the RMPI1640 medium comprising 10% fetal bovine serum at 37° C., 5% CO$_2$ and 100% humidity.

The cytotoxic activity testing was carried out by the standard MTT-test using 96-well plates. Seeding density of cells was 5,000 cells in a well. The cells K562 and A549 were incubated with the complexes I and II at concentrations 1 μM, 10 μM or 100 μM for 72 hours.

MTT-test is based on the capability of dehydrogenases of live cells to reduce unstained MTT-reagent to the blue crystals of formazan crystals soluble in dimethylsulfoxide (DMSO). The optic absorption of stained DMSO solutions was measured on an automated counter. The cytotoxic activity was assessed in percent by the survival of the cells and calculated according to the formula: (mean value of optic absorption in test samples/mean absorption in the control)×100. IC$_{50}$ was determined by a "dose-effect" curve.

The cytotoxic activity examination of nitrosyl iron complexes I and II on line K562 and A549 cells revealed a direct relationship between the survival of cells and concentration of I and II. IC$_{50}$ value for I was 50 μM and 100 μM—for II.

Apoptotic Activity Study of Water-soluble Iron Complexes on Cancer Cells

A method for determining activity of caspases is based on the use of fluorochromic inhibitors of caspases (FLICA). These inhibitors are capable of penetrating into a cell while not being cytotoxic. Within the cell FLICA-inhibitor is covalently bound to active caspase. A labeled inhibitor of caspases (carboxyfluorescein fluoromethyl keton peptide) is used for reagents (kits) exhibiting fluorescence in the green spectrum band.

The freeze-dried reagent FAM-DEVD-FMK for determining caspase-3 and caspase-7 was experimentally used to test apoptotic cells. When FAM-DEVD-FMK is added to a cellular population of cells, it penetrates into each cell wherein covalent binding thereof to a large subunit of an active caspase heterodimer occurs and thus, it inhibits enzymatic activity. The reagent covalently bound to the enzyme remains inside the cell. A portion of the unbound reagent diffuses from the cell and can be removed by washing. Residual green fluorescent signal directly depends on an amount of active caspase enzymes, which were present in the cell at a moment of adding the reagent.

Process reagent solution was prepared by adding 50 μl DMSO (150× test) and then 200 μl phosphate buffer solution until obtaining 30× test to the freeze-dried reagent FAM-DEVD-FMK.

10× buffer for washing cells provided by the ICT firm was used to remove the unbound reagent FAM-DEVD-FMK. 1× buffer diluted with distilled water was used for the experiments.

Cells for the experiments were seeded into flasks at density 500 thousand cells in one milliliter. Induced cells were prepared by incubation for 75 hours with nitrosyl complexes I and II in equimolar concentration 50 µl that is close to $IC_{50}$ for all the complexes.

Non-induced unstained cells and FLICA-cells as well as induced unstained cells were used as a negative control.

Upon termination of incubation term, the cells were centrifuged for 5 minutes at 1,200 rpm at room temperature (RT). Pellet was re-suspended in 300 µl medium, 10 µl 30× FLICA were added and the mixture was incubated for 1 hour at 37° C. and 5% $CO_2$. Upon termination of incubation, samples were centrifuged, supernatant was discarded. Then pellet was washed twice with 1× buffer (2 ml and 1 ml). Pellet was re-suspended in 900 µl 1× buffer. Sample aliquots of induced and non-induced cells were taken, 2 µl reagent propidium iodide (PI) ready for use were added and the mixture was incubated at RT for 10 minutes to stain dead cells.

Fluorescence of all cell specimens was analyzed on a liquid citometer Backton Dikenson Fascaliber using a laser with 488 nm wavelength. Results were obtained in the form of fluorescent signal distribution of stained cells in the channel FL1 (FLICA green band) and FL3 (PI red band). In a left lower quadrant live cells were determined; in a right lower quadrant positive FLICA cells (FLICA+) were determined; in a left upper quadrant stained PI cells were determined, and in a right upper quadrant stained PI and FLICA+ cells were determined. A graphic presentation of cells in the channels was obtained using the Dot-Plot software. Results were quantitatively assessed using version 2/8 of the software WinMDA and expressed in the form of the content of stained and unstained cells relative to a total amount of cells in percent.

Figure 7:
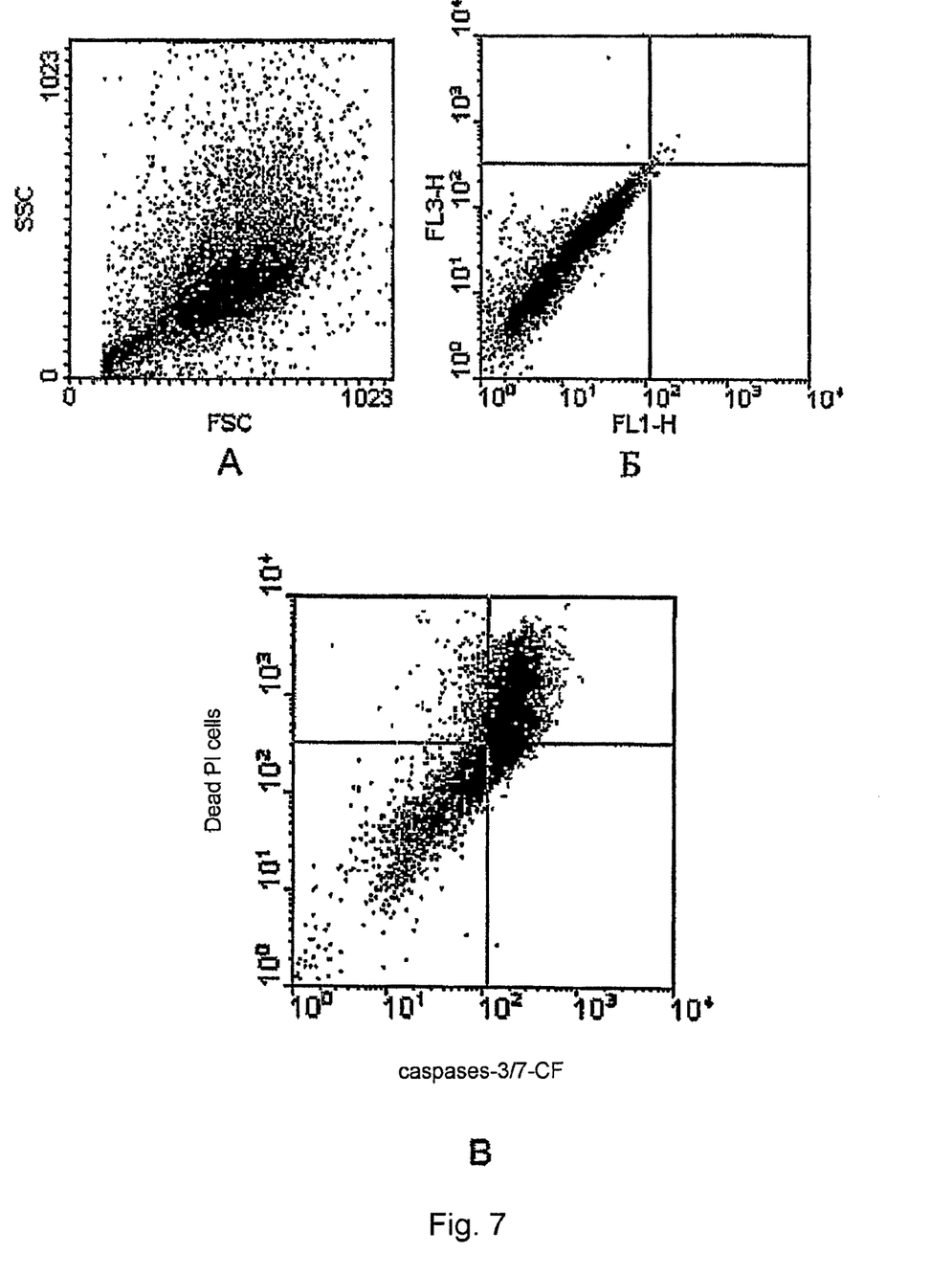
FIG. 7 represents analysis of fluorescent signal in I-50 induced cells: A is a graphic representation in coordinates of a direct (FSC) and transverse (SSC) light scattering of the induced non-stained cells of the K-562 line (control); B represents autofluorescence of the induced non-stained cells; C represents fluorescence of the induced stained cells.

Nitrosyl complex I studied exhibited capability of initiating caspase 3 and 7 activity and thus, of inducing apoptosis in line K562 cells of human erythroblast leukemia. At the same time, 77% cells in apoptosis were recorded in the presence of complex I (FIG. 7).

The invention claimed is:

1. Binuclear cationic nitrosyl iron complex with natural aliphatic thiolyls of general formula $[Fe_2(SR)_2(NO)_4]SO_4$, wherein R is sulfur-containing aliphatic ligands of natural origin.

2. Binuclear cationic nitrosyl iron complex according to claim 1, wherein R is cystamine or penicillamine.

3. A method for the preparation of binuclear cationic nitrosyl iron complexes according to claim 1 consisting in that aqueous iron (II) sulfate solution is treated with a corresponding water-soluble thiol-amine in the presence of gaseous NO in an acidic medium.

4. The method according to claim 3 characterized in that the process is carried out at room temperature, advantageously at 18-25° C.

5. The method according to claim 3 characterized in that the process is carried out in an oxygen-free atmosphere.

6. The method according to claim 3 characterized in that cystamine or penicillamine is used as a thiol-amine.

7. A donor of nitrogen monoxide that is the binuclear cationic nitrosyl iron complex according to claim 1.

8. An apoptosis inducer of cancer cells which is the binuclear cationic nitrosyl iron complex according to claim 1.

9. A pharmaceutical composition comprising an effective amount of the binuclear cationic nitrosyl iron complex according to claim 1 and a pharmaceutically acceptable carrier.

10. The pharmaceutical composition according to claim 9, wherein a proton-containing medium is used as the pharmaceutically acceptable carrier.

11. The pharmaceutical composition according to claim 10, wherein water, normal saline solution, water-soluble biopolymers are used as a proton-containing medium.

12. The pharmaceutical composition according to claim 9, wherein the binuclear cationic nitrosyl iron complex is present in an amount of 50-100 µM.

13. A kit useful for the treatment of cancer diseases comprising (1) a pharmaceutical composition comprising a binuclear cationic nitrosyl iron complex according to claim 1 in a sealed package, and (2) auxiliary components.

* * * * *